United States Patent
Savaides et al.

(10) Patent No.: US 12,083,211 B2
(45) Date of Patent: Sep. 10, 2024

(54) METHODS OF INCREASING THE VOLUME OF A FIBER, SUCH AS MAMMALIAN HAIR, AND/OR ALTERING THE STRUCTURE OF A FIBER WITH A CHITOSAN POLYELECTROLYTE COMPLEX

(71) Applicant: Henkel AG & Co. KGaA, Duesseldorf (DE)

(72) Inventors: Andrew Savaides, Stamford, CT (US); Rushi Tasker, Stamford, CT (US); Mona Vaidya, Stamford, CT (US); Jasmine Martich, Stamford, CT (US)

(73) Assignee: HENKEL AG & CO. KGAA (DE)

( * ) Notice: Subject to any disclaimer, the term of this patent is extended or adjusted under 35 U.S.C. 154(b) by 0 days.

(21) Appl. No.: 16/917,087

(22) Filed: Jun. 30, 2020

(65) Prior Publication Data
US 2021/0401720 A1 Dec. 30, 2021

(51) Int. Cl.
| | | |
|---|---|---|
| *A61K 8/34* | (2006.01) | |
| *A61K 8/65* | (2006.01) | |
| *A61K 8/73* | (2006.01) | |
| *A61Q 5/06* | (2006.01) | |

(52) U.S. Cl.
CPC .............. *A61K 8/736* (2013.01); *A61K 8/347* (2013.01); *A61K 8/65* (2013.01); *A61Q 5/06* (2013.01)

(58) Field of Classification Search
CPC .......... A61K 8/736; A61K 8/347; A61K 8/65; A61Q 5/06
See application file for complete search history.

(56) References Cited

U.S. PATENT DOCUMENTS

2017/0360679 A1 * 12/2017 Savaides

OTHER PUBLICATIONS

Definition of "room temperature" (New World Encyclopedia, Accessed from https://www.newworldencyclopedia.org/entry/room_temperature, accessed on Oct. 23, 2021, pp. 1-5) (Year: 2021).*
PubChem Compound Summary 2-Methylundecanal (Accessed from https://pubchem.ncbi.nlm.nih.gov/compound/2-Methylundecanal , Accessed on Dec. 5, 2022, pp. 1-4) (Year: 2022).*

* cited by examiner

*Primary Examiner* — Alma Pipic
(74) *Attorney, Agent, or Firm* — Calderone McKay LLC

(57) ABSTRACT

The invention includes methods of increasing the volume of a fiber by applying to the fiber a chitosan cross linked with or complexed to an aldehyde-bearing compound, and a polyanion. The fiber is then dried forming a chitosan polyelectrolyte complex on the hair that increases the dimension of the fiber. The fiber may be wet prior to application and may be a mammalian hair. Also included are method of semi-permanently altering the structure of hair that includes topically applying to hair a chitosan cross linked with or complexed to an aldehyde-bearing compound, and a polyanion. Also contemplated within the scope of the invention is a hair care polyelectrolyte complex that includes a chitosan cross linked with or complexed to an aldehyde-bearing compound, and a polyanion. Systems for hair treatment are also encompassed within the scope of the invention and include at least two formulations: a first formulation comprising a chitosan cross linked with or complexed to an aldehyde-bearing compound, and a second formulation comprising a polyanion. Such systems may be included in hair care kits.

16 Claims, 1 Drawing Sheet

| 20 Volume Hair | Initial (after 1X) | | After 3X | | After 6x | |
|---|---|---|---|---|---|---|
| Attributes | Treated | Untreated | Treated | Untreated | Treated | Untreated |
| Volume -Fullness | 4 | 3 | 3.80 | 3 | 3.7 | 3.1 |
| Body Thickness | 3.8 | 3 | 4.00 | 3 | 4 | 3.0 |
| Root Lift | 4 | 2.5 | 4 | 3.5 | 3.8 | 3 |
| Side Body | 4.20 | 3 | 4 | 3 | 3.8 | 3 |
| Style Definition | 4 | 2.50 | 3.5 | 3 | 3.65 | 3.5 |
| Wet Combing | 4 | 4 | 4 | 4 | 4 | 4 |
| Dry Feel-Softness | 3 | 4 | 4 | 4 | 4 | 4 |
| Shine/ Luster | 3.50 | 3 | 3.5 | 3.50 | 3.5 | 3.5 |
| Overall | 4 | 2.50 | 4 | 3 | 3.75 | 3 |

METHODS OF INCREASING THE VOLUME OF A FIBER, SUCH AS MAMMALIAN HAIR, AND/OR ALTERING THE STRUCTURE OF A FIBER WITH A CHITOSAN POLYELECTROLYTE COMPLEX

BACKGROUND OF THE INVENTION

Chitosan is a derivative of chitin, a compound usually isolated from the shells of crustaceans such as crab, lobster and shrimp. Chitosan is the soluble form in aqueous acidic solutions or partially the deacetylated derivative of chitin, i.e., it consists of α (1~4)-linked 2-acetamido-2-deoxy-β-D-glucopyranose and 2-amino-2-deoxy-~D-glucopyranose residues. Chitin and chitosan are abundant, renewable and sustainable polymers and have excellent properties such as, biodegradability, bio-compatibility, non-toxicity, and adsorption to hair, skin and nails. Most chitosans are derived from crustacean shells; they therefore can be marketed as "natural" to consumer products end users.

Chitosan has a cationic nature due to the protonation of amino groups on the polymer backbone and becomes a cationic polyelectrolyte upon dissolution in most aqueous formulations. Many fibers included textile fibers like cotton and wool and mammalian hair/furs are negatively charged and are capable of complexing with chitosan alone to fix or smooth hair. However, chitosan treatment alone of hair and fibers do not provide satisfactory increases in hair body and volume, and although it is capable of coating hair, the resulting coating becomes sticky over time, resulting in hair that looks and feels weighted down, limp and unclean.

There remains in the art a need for a methods of treating hair that provides increased volume and body to the without the disadvantages of a sticky residue and which can also contribute to the hair's smoothness.

BRIEF SUMMARY OF THE INVENTION

The invention includes methods of increasing the volume of a fiber by applying to the fiber a chitosan cross linked with an aldehyde-bearing compound, and a polyanion. The fiber is then dried forming a chitosan polyelectrolyte complex on the hair that increases the dimension of the fiber. The fiber may be wet prior to application and may be a mammalian hair. Also included are method of semi-permanently altering the structure of hair that includes topically applying to hair a chitosan cross linked with an aldehyde-bearing compound, and a polyanion. The structural alteration persists on the hair after about 1 to about 10 washings. Also contemplated within the scope of the invention is a hair care polyelectrolyte complex that includes a chitosan crosslinked with an aldehyde-bearing compound, and a polyanion.

Systems for hair treatment are also encompassed within the scope of the invention and include at least two formulations: a first formulation comprising a chitosan cross linked with or complexed to an aldehyde-bearing compound, and a second formulation comprising a polyanion. Such systems may be included in hair care kits, such kits further including various related accessories and/or hair care tools, such a glove or gloves, a hair clip, a dryer, a towel, a timer, a swab, a spray bottle or atomizer, a brush, a cap, a comb, a roller, a pin, and a mirror.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 shows a comparison of the hair attributes observed before and after treatment.

DETAILED DESCRIPTION OF THE INVENTION

The invention described herein includes methods of increasing the volume or body of a fiber, such as a mammalian hair, and/or methods of altering the structure of the hair. Also included are hair care chitosan polyelectrolyte complexes that increase the volume/body of hair and/or alter the structure of hair as well as hair treatment systems for forming or which contain the complexes, and related kits. Such methods, complexes, systems and kits may also be used in textile applications to treat, process, condition or conserve textile fibers or textile tissues, especially natural textile fibers, such as wool, leather, linen, fur, silk, hemp, flax, cottons, keratin, bamboo, an anionically charged synthetic fiber, a plant derived fiber and the like. The terms "fiber" and "hair" are used interchangeably herein.

By "increasing the volume or body of a fiber" it is meant that a dimension of the hair is increased by an amount, for example an increase in the circumference of the hair or fiber, such that when the hairs are grouped together in, for example, a tress or a "head" of hair, a volume increase can be observed when measured by the protocols commonly used in the art, for example, the Polarizing Imaging Method (PIM) of N. Lechochinski and S. Breugnot, J. Cosmet. Sci., March/April 2012. The PIM method is executed using the Bolero Lite system and is described in more detail below.

The Bolero Lite System from Bossa Nova Vision of Los Angeles California can be used for volume evaluation and frizz analysis. It is an imaging system dedicated to quickly give quantitative data on the volume of hair and can discriminate the fly-away/frizz from the bulk of hair swatches on a 2D image using light transmission variations to evaluate hair density. It provides product efficacy of volumizing products to basic analysis of hair swatch volume and visual appearance. It provides efficiency and precision in the measurements of hair volume for an optimal user. The system allows the reconstruction of the 3D volume of hair swatches. Based on the acquisition of a sequence of contours, Bolero delivers the 3D model of the hair swatch, permitting the simultaneous measurement of the hair swatch volume and the analysis of fly-aways.

Other methods of evaluating hair tresses based on 2D imaging are described by Jane Clark, C. Robbins and C. Reich in the J. Society of Cosmetic Chemists, 1991, 42. Other quick but semiquantitative method of evaluating volume includes the 2-dimensional expansion of hair swatches and evaluation of the fiber diameter before and after treatment using laser micrometry.

Additionally, methods, complexes, systems and kits of the invention may be used to alter the structure of the hair. By "alter the structure" it is meant to modify one or more observable aspect of the hair, such as to make it less frizzy, less fine, to increase smoothness, to reduce "fly aways", to increase shine and luster, to increase softness, to increase resistance to humidity, to hold curl or wave, etc. "Hair", in the context of this method and in contrast to "a hair" or "the hair" means a field or grouping of hair, such as for example, a live head of hair, a tress of hair, a wig of hair, a fur bearing pelt, pelt, a mammalian coat, and portions or areas thereof and similar.

The observable alterations can be evaluated by comparing untreated hair with treated hair using various evaluation protocols as in known in the art and/or in some instance, simple observation. For example, salon half head testing evaluation has been carried out following below directions for volumizing or smoothing effects on hair with Poly Electrolyte Complexes (PEC) as follows: Shampoo Hair with Clarifying Shampoo and towel blot hair excess moisture. Apply the polyanion solution only to root area (~1-2 inches from scalp) for 1-2 minutes. Apply the chitosan/vanillin composition to hair from root to ends. Once the product has been applied, work with fingers and dry hair to 80% 5. Style hair focusing on the roots and blow drying upwards (away from scalp) motion using a round brush or fingers. The effect of the treatment has been evaluated initially, after one, two, three and six shampoos.

Additionally, or alternatively, one me evaluate the effect of 'smooth hair' as follows: Shampoo Hair with Clarifying Shampoo and towel blot hair excess moisture. Apply the ready PEC product generously making sure that all the hair fibers are fully saturated. Work through with fingers and comb hair with wide tooth comb. Cover hair with or without cap for 10-15 minutes. Towel blot excess product and blow dry hair with high heat using small sections with fingers or a paddle brush. The effect of the treatment has been evaluated initially, after one, two, three and six shampoos.

The methods employ use of a hair care polyelectrolyte complex that includes a chitosan crosslinked with an aldehyde bearing compound (hereinafter "chitosan/ABC") complexed with a polyanion to form a hair care polyelectrolyte complex. Such complexing may occur prior to application to the hair, or in situ on the hair, if the chitosan/ABC and the polyanion are applied separately.

For formation of the hair care polyelectrolyte complexes of the invention, any chitosan may be used. In an embodiment, it may be preferred that chitosan having a deacetylation of about 50% to about 100%, about 60% to about 80% and about 70% to about 95% is used, and molecular weights of about 50,000 to about 1,000,000 g/mole, about 300,000 to about 2,000,000 g/mole and about 500,000 to about 5,000,000 g/mole. In an embodiment, a chitosan having a molecular weight of about 300,000 to about 2,000,000 g/mol and deacetylation of about 70% to about 90% may be preferred.

The selected chitosan(s) are crosslinked with an aldehyde bearing compound ("ABC"). By "ABC" it is meant any compound having one or more aldehyde functional groups that are available to react with the nitrogen atoms of chitosan to form one or more reactive imine covalent bonds crosslinking with hair reactive sites. In some embodiments, it may be preferred that the ABC is a phenolic aldehyde, such as, for example, vanillin, p-vanillin, o-vanillin, ethylvanillin and similar compounds.

Other suitable ABCs may include, for example without limitation, benzaldehyde, formaldehyde, acetaldehyde, (R)-carvone, cinnamaldehyde, glyoxylic acid, 3-methyl-3 phenyl glycidic acid ethyl ester, acetaldehyde, capraldehyde, piperonal citral, undecanal, octanal, heptanal, nonanol, dodecanal, ethyl 3-(4-methylphenyl)oxirane-2-carboxylate, unadecalactone, oleic aldehyde, glyoxal, glutaraldehyde, and methyl nonyl acetic aldehyde. Combinations of different ABCs may also be used.

In the practice of the invention the chitosan/ABC crosslinked moiety may be complexed to, or is capable of forming a complex with, a polyanion. Suitable polyanions include, for example, water soluble, natural anionic polysaccharides, synthetic anionic polymers, synthetic anionic copolymers, anionic proteins, oxidized proteins, anionic silicones, anionic surfactants or amphoteric surfactants. Anionic surfactants that have $SO_3^-$, $SO_4^-$ and $COO^-$ functional groups may also be used.

Further suitable polyanions may include, without limitation:
(i) Synthetic polymers: such as polyacrylic acid, polystyrene sulfonate, acrylate copolymers, polyaspartate, sodium cetearyl sulfate, sodium lauroyl glutamate, glyceryl stearate, acrylamide/sodium acryloyldimethyltaurate/acrylic acid copolymer, acrylates/methoxy PEG-10 maleate/styrene copolymer, sodium acrylates/beheneth-25 methacrylate crosspolymer (and) hydrogenated polydecene (and) lauryl glucoside, dimethiconol (and) TEA-odecylbenzenesulfonate, acrylates/steareth-20 methacrylate copolymer, dehydroxanthan gum, dimethicone PEG-7 phosphate;
(ii) Anionic surfactants: such as alkyl ether sulfates, sulfonic acids, isethionates, sulfosuccinates and sulfosuccinamates, alkyl sulfates, glyceryl esters and derivatives of the same, sarcosinates and sarcosine derivatives, sodium laureth sulfate, sodium $C_{14-16}$ olefin sulfonate, sodium laureth sulfate, sodium lauryl sulfate, ammonium laureth sulfate, sodium sauroyl glycinate, sodium methyl cocoyl taurate, dodecylbenzene sulfonic acid (and) water, glyceryl stearate citrate, disodium cocoyl glutamate, TEA-cocoyl alaninate, sodium $C_{14-16}$ olefin sulfonate, dimethiconol (and) TEA-dodecylbenzenesulfonate, sodium methyl cocoyl taurate, sodium coco-sulfate, sodium cocoyl isethionate, sodium coco-sulfate, sodium methyl lauroyl taurate, disodium cocoamphodiacetate, TEA-cocoyl glutamate;
(iii) Anionic Silicones: such as dimethiconol (and) TEA-dodecylbenzenesulfonate (e.g., XIAMETER™ MEM-1788 emulsion from Dow Inc.), dimethiconol (e.g., BELSIL® DM 3112 VP available from Wacker Chemie AG), dimethicone PEG-7 phosphate (e.g., PECOSIL® PS-112 available from Wacker Chemie AG);
(iv) Anionic Natural Polymers (Biopolymers): natural gum arabic, xanthan gum, biossacharide gum-4, carrageenan (I, k and λ), alginic acid, pectin, lactobionate, hyaluronic acid, heparin, soybean-soluble polyssacharide, hydroxypropyl guar, carboxymethyl hydroxypropyl guar, carboxymethyl guar, 18-MEA, cholesterol sulfate; and
(v) Anionic Proteins: such as keratin, oxidized keratin, hydrolyzed keratin, keratin derivatives, such as those commercially available from Croda Personal Care International Pcl under the trade names KERATEC™ IFP-HMW, KERATEC™ NKS, KERATEC™ PEP, KERATEC™ IFP, and cocoyl hydrolyzed collagen.

In some embodiments, it may be preferred that the polyanion is chosen from a sulfo/sulfonate bearing polymer, the salts of poly(acrylic acid), salts of poly(methacrylic acid), salts of poly(L-lysine citramide), salts of poly(styrene sulfonic acid) and mixture thereof. The salt may be a sodium salt or a potassium salt. In these embodiments the sulfo/sulfonate bearing polymer is, for example, polystyrene sulfonate or a copolymer of acrylic acid/acrylamidomethyl propane sulfonic acid.

If one desires a natural polymer or biopolymer for use as the polyanion, use of keratin, hydrolyzed keratin, oxidized keratin, keratin derived materials, natural gum arabic, xanthan gum, biossacharide gum-4, carrageenan (I, k and λ), alginic acid, pectin, lactobionate, hyaluronic acid, heparin, soybean-soluble polyssacharide, hydroxypropyl guar, carboxymethyl hydroxypropyl guar, carboxymethyl guar, 18-MEA, cholesterol sulfate, hydrolyzed collagen or mixtures of the same may be preferred.

In an embodiment, a mixture of any polyanions listed herein or known in the art may be employed.

In the practice of the invention, the chitosan/ABC and selected polyanion is topically applied to the hair or fiber; such applicant may be in two steps so the hair care polyelectrolyte complex is formed in situ on the hair or fiber. Alternatively, the chitosan/ABC polyanion hair care polyelectrolyte complex may be formed in advance of application to the hair. In either case, one may prefer that the hair is wetted with water or an aqueous solution prior to the application.

If the chitosan/ABC and selected polyanion are maintained separately prior to application, the application of the two may be accomplished in two steps, or application may be carried out substantially simultaneously. In an embodiment, each of the chitosan/ABC and the polyanion is carried in a formulation, and the chitosan/ABC formulation is applied as a first treatment, followed substantially immediately by application of the polyanion formulation. In another embodiment, the treatments are reversed. Alternatively, the chitosan/ABC formulation and the polyanion formulation are may be mixed by the end user just prior to application to the hair (e.g., 30 seconds to 30 minutes prior to application to the hair).

In a different version of the method, the chitosan/ABC and the polyanion are provided to the end user in a single formulation. In such instance the hair care polyelectrolyte complex may be formed in advance of its application to the hair.

Each formulation described may independently contain additional additives as described in more detail below.

Application of the chitosan/ABC and polyanion may be carried out by any means in the art, including, for example, combing, wiping, smudging, painting, smearing, blotting, soaking, and spraying. For better results in an embodiment, the application is carried out in a manner that provides even and uniform distribution of the formulation(s) throughout the hair treatment area.

The amount applied may vary depending on the surface area of hair to be covered and the end effect desired. As an example, on average, one may apply about 2.5 to about 3 fl oz per head of hair. An exemplary minimum application may be about 1.5 to about 2 fl oz per head.

The hair is then dried; heat is not required. It may be preferred that the hair is dried by application of room temperature (about 21° C.) or tepid warm air from a fan, hairdryer or the ambient environment. In an embodiment, the preferred drying temperature may be about X to about Z. If the hair treatment area is more than one hair, such as a "head" of hair or a hair tress, drying may be carried out using various hair care tools in methods known in the art to encourage volumization, such as roll brushes and Velcro curlers.

The chitosan/ABC and selected polyanion may be delivered together or separately to the hair in a treatment formulation; preferably such formulations are water based and/or substantially aqueous. The formulations may contain other additives that are commonly included in hair care and personal care compositions, such as, for example, humectants, colorants, dyes, acidulants, fragrances, pH modifiers, sensates, metal chelators, pigments, oil, waxes, alcohols, surfactants, UV filters or blockers, light reflectants or dispersants, glitter, conditioners, silicones, humectants, antistatic agents, preservatives, pollution shielding compounds, a pheromone, a polymeric dye, a conditioner, a thickener, an insect repellent, an acid, a base, a salt, a charge density adjusting agent, a solubility enhancing agent, a deposition aid, and/or a dispersing agent.

In embodiments of the invention, it may be preferred that the final pH of the formulation that contains the chitosan/ABC, the polyanion and/or the hair care polyelectrolyte complex is about 3.0 to 8.0 or about 3.5 to about 4.5 or 5.0. In some embodiments, a pH of 3.8 may be preferred. To arrive at the desired pH, various alkali compounds may be added to the formulation as is known in the art. Such alkali compounds may include ammonia, sodium hydroxide, potassium hydroxide, monoethanolamine, diethanolamine, diisoproanolamine, triethanolamine, and isopropanolamine.

In an embodiment, the chitosan is crosslinked to the ABC, e.g., the vanillin or p-vanillin, in a 4:1 ratio, a 3:1 ratio, or a 2:1 ratio (w/w %), although other ratios can be used and may vary depending on the specific types of chitosan and/or ABC used and their specific reactivities. Such crosslinking may occur prior to application to the hair, in situ on the hair or both.

In various embodiments of the invention, it may be preferred that the chitosan/ABC is present in the formulation in an amount of, without limitation, about 0.2% by weight to about 1.5% by weight, about 0.4% by weight to about 1% by weight, about 0.6% by weight to about 0.8% by weight (each % by weight of the total formulation). The polyanion, for example, may be present in an amount of about 0.05% by weight to about 2% by weight, about 0.7% by weight to about 1.5% by weight, about 1% by weight to about 1.4% by weight (each % by weight of the total formulation).

The formulation(s) may be independently prepared in any product format desired or known in the art. For example, it may take the form of a liquid, semi-liquid, gel, spray, mist, foam, mousse, paste, crème, emulsion and the like. In some embodiments, the formulation is prepared as a loose or compressed powder, granules, pellets, etc., to which the end consumer or the distributor may add a liquid or semi-liquid solvent or carrier. The formulations may be presented to the end user in the format of "leave on" treatments, "leave on" conditioners, "rinse off" conditioners, shampoos, stylers and the like.

Use of the methods and hair care polyelectrolyte complexes described herein may provide to the hair an increase in dimension and/or the alternation of the observable structure of the hair that persists on a semi-permanent basis. By semi-permanent it is meant, for example, that the effect(s) (e.g., volumizing or smoothing) is observable after the hair is washed in a conventional manner at least once, twice or three times or more. For example, the effects may be observable for about 3 to about 20 washings, for about 5 to about 15 washings, for about 8 to about 12 washings. Advantageously, the degree of permanency (e.g., 3 washings versus 20 or more) can be adjusted by routine modifications to the formulation or application by which the hair care polyelectrolyte complex is delivered to the hair.

Use of the methods and hair care polyelectrolyte complexes described herein may provide to the hair an increase in its ability to bind hairs dyes strongly, thereby reducing the dyeing time, and increasing the saying power of the dye over time (e.g., less rapid fading of hair color as compared to untreated, dyed hair). The adsorption and crosslinking of the inventive complex on hair has a net cationic charge. This film will attract as a magnet anionic, acid dyes and bind them strongly and fast on the hair surface. This strong attraction efficiently bind these dyes on hair fast at low pH without damaging the hair with long lasting results. See, for example, Magnetically Responsive Textile for Preconcentration of acid food dyes, Material Chemistry and Physics, January 2019. Acid dyes with which this effect can be enjoyed may include anthraquinone, azo and triphenyl methane dye types such as Acid Black 1, Acid Yellow 36, Acid Yellow 23, Acid Blue 117, Acid Blue 4, Acid Orange 19, Acid Blue 25, Acid Orange 3 and mixtures thereof.

Also included in the invention are various hair treatment kits. Such kits may include "communication devices" that provide information related to the use of the contents of the kit, such as instructions. These devices may take any form, such as a writing, video, audio, directions to website, podcast or videocast, etc. The kits may also include one or more accessories or tools useful in the use or application of the contents of the kit or hair care generally. Such accessories can include, for example, gloves, a hair clip, a dryer, a towel, a timer, a swab, a spray bottle or atomizer, a brush, a comb, a roller, a pin, and a mirror.

EXAMPLES

Example 1—Preparation of a Hair Treatment Formulation Containing Chitosan/Vanillin A formulation containing chitosan crosslinked to vanillin for use in the methods of the invention was prepared by combining the components in the amounts as set forth in Table A, below.

TABLE A

Chitosan/vanillin formulation (1:4) at pH 4

| Component | Amount (w/w %) |
|---|---|
| Chitosan high density | 0.60 |
| Vanillin | 0.15 |
| Acetic acid | 1.00 |
| diazolidinyl urea (and) iodopropynyl butylcarbamate (and) propylene glycol | 0.40 |
| Fragrance | 0.10 |
| PPG-26-buteth-26 (and) PEG-40 hydrogenated castor oil (and) water | 0.20 |
| Water Q.S. | 100 |
| pH Q.S. | 4.00 |

Example 2—Preparation of a Hair Treatment Formulation Containing the Polyanion Sodium Polystyrene Sulfonate A formulation containing the polyanion sodium polystyrene sulfonate for use in the methods of the invention was prepared by combining the components in the amounts as set forth in Table B, below.

TABLE B

Polyanion formulation at pH 7

| Component | Amount (w/w %) |
|---|---|
| Sodium polystyrene sulfonate (Flexan II) | 1.00 |
| Diazolidinyl urea (and) iodopropynyl butylcarbamate (and) propylene glycol | 0.50 |
| Water Q.S. | 100 |
| pH Q.S. | 7.00 |

The volumizing effect of the method of the invention was confirmed by treatment and evaluation of nine "half heads" of hair.

The hair was treated as follows: Each was shampooed using a standard clarifying shampoo in the conventional manner. Hair was towel blotted to remove excess water. The formulation of Example 2 (Table B) was applied to root area (2 inches from scalp) and allowed to process for one minute. The formulation of Example 1 was applied to hair from root to ends.

Hair was then dried in an upwards direction using a household hair dryer set at low heat to about 80% dryness with brush; cool air is then "blasted" from the dryer to cool the hair. The salon half head evaluation results below for initial, after 3 and 6 shampoos on 9 models with tinted and fine tinted hair. The evaluation rating ranged from 0-4 for all attributes.

FIG. 1 shows a comparison of the hair attributes observed before and after treatment. The hair showed a volume increase from a single treatment that lasted 5-6 shampoos or more as compared to untreated hair. The initial volume effects included root lift, more side and frontal volume. These effects did not diminish during the entire day and no support styling products were necessary to maintain or preserve the volumizing effect.

The volumizing effect was also confirmed on hair swatches using the Bolero lite method described above. The total increase of initial hair volume was 75.19% (p=0.0083). This increase in total volume is from the complex formation as 44.87% increase by the chitosan-Van and 30.32% from the flexan representing the ABC complex.

Example 3—Preparation of the Chitosan/Vanillin/Sodium Polystyrene Sulfonate (Flexan II) Complex The complex is prepared in a formulation to be used as a "one step" application on hair as a leave-in volumizing treatment. The formulation was prepared by combining the components in the amounts as set forth in Table C, below.

TABLE C

Chitosan/Vanillin/Flexan II complex solution

| Component | Amount (w/w %) |
|---|---|
| Chitosan High Density | 0.30 |
| anillin | 0.075 |
| Acetic acid | 0.14 |
| Sodium polystyrene sulfonate (Flexan II) | 0.20 |
| diazolidinyl urea (and) iodopropynyl butylcarbamate (and) propylene glycol | 0.40 |
| Cetrimonium Chloride and Water | 0.75 |
| Fragrance | 0.10 |
| PPG-26-buteth-26 (and) PEG-40 hydrogenated castor oil (and) water | 0.20 |
| Water Q.S. | 100 |
| pH Q.S. | 4.50 |

Example 4—Preparation of Chitosan/Vanillin/Polymer CG 4500 Complex as a Hair Smoothing Treatment The formulation was prepared by combining the components in the amounts as set forth in Table D, below.

TABLE D

Chitosan/Vanillin/Polymer CG 4500 complex solution

| Component | Amount (w/w %) |
|---|---|
| Chitosan High Density | 0.15 |
| Vanillin | 0.04 |
| Acetic acid | 0.14 |
| Arylic Acid/Acrylamido methyl Propane Sulfonic Acid Copolymer (Polymer CG 4500) | 0.15 |
| diazolidinyl urea (and) iodopropynyl butylcarbamate (and) propylene glycol | 0.40 |
| Cetrimonium Chloride and Water | 0.75 |
| Fragrance | 0.10 |
| PPG-26-buteth-26 (and) PEG-40 hydrogenated castor oil (and) water | 0.20 |
| Water Q.S. | 100 |
| pH Q.S. | 3.50 |

The Chitosan/Vanillin/Polymer CG 4500 complex solution and was evaluated in the salon as a smoothing treatment on curly hair type II, following the below testing protocol:

Washing hair with a Clarifying Shampoo and towel blotting excess moisture. Apply the Chitosan/Vanillin/Polymer CG 4500 complex solution generously making sure that all the hair fibers are fully saturated. Working through with fingers and comb hair with wide tooth comb, covering hair with or without cap for 10-15 min. Towel blot excess product, and blow dry hair with high heat using small sections with fingers or a paddle brush in the downward or same direction of the cuticles. Shampoo and condition hair after 24 hours. The effect of the treatment is shown on Table E after the hair was shampooed and conditioned 3 times.

TABLE E

Curly Hair Type I- II -After 3X

| Attributes | Treated | Untreated |
|---|---|---|
| Fiber Alignment | 4 | 2.5 |
| Smoothing | 4 | 2.5 |
| Wet Combing | 3.5 | 3.0 |
| Wet Feel - After Comb | 3.5 | 3.0 |
| Dry Feel - Softness | 3.5 | 3.0 |
| Dry Feel -Smoothness | 4.0 | 3.0 |
| Fly Away | 4.0 | 3.0 |
| Shine/Luster | 3.5 | 2.5 |
| Overall | 4.0 | 2.5 |

Example 5—Preparation of a Hair Treatment Formulation Containing Chitosan/Vanillin/Keratin Complex The formulation was prepared by combining the components in the amounts as set forth in Table F, below.

TABLE F

Chitosan/Vanillin/Keratec IFP-HMW complex solution

| Component | Amount (w/w %) |
|---|---|
| Chitosan High Density | 0.25 |
| Vanillin | 0.063 |
| Acetic acid | 0.15 |
| Keratin and Water (Keratec IFP -HMW) | 1.46 |
| Diazolidinyl urea (and) iodopropynyl butylcarbamate (and) propylene glycol | 0.40 |
| Cetrimonium Chloride and Water | 1.0 |
| Fragrance | 0.10 |
| PPG-26-buteth-26 (and) PEG-40 hydrogenated castor oil (and) water | 0.20 |
| Water Q.S. | 100 |
| pH Q.S. | 3.50 |

The Chitosan/Vanillin/Keratin complex solution and was evaluated in the salon as a smoothing treatment on curly hair type II, following the below testing protocol:

Washing hair with a Clarifying Shampoo and towel blotting excess moisture. Apply the Chitosan/Vanillin/Keratin complex solution generously making sure that all the hair fibers are fully saturated. Working through with fingers and comb hair with wide tooth comb, covering hair with or without cap for 10-15 min. Towel blot excess product, and blow dry hair with high heat using small sections with fingers or a paddle brush in the downward or same direction of the cuticles. Shampoo and condition hair after 24 hours. The effect of the treatment after 3 shampoos and conditioners is shown on Table G.

TABLE G

Curly Hair Type I-II After 3X

| Attributes | Treated | Untreated |
|---|---|---|
| Fiber Alignment | 3.5 | 2.5 |
| Smoothing | 4 | 3 |
| Wet Combing | 3.5 | 3.0 |
| Wet Feel - After Comb | 3.0 | 2.5 |
| Dry Feel - Softness | 3.0 | 2.5 |
| Dry Feel -Smoothness | 3.0 | 2.5 |
| Fly Away | 4.0 | 3.0 |
| Shine/Luster | 4.0 | 2.5 |

The complex formation between the Chitosan/Vanillin with seaweed derived linear polysaccharides thickeners, such as alginates and carageenans show strong conformational changes in solution. The changes are bulk effects increasing viscosity and stabilizing the gel networks in solution of these linear polysaccharides. The complexation results into an increase in the gel strength and rheology of these thickeners. The complex formation increases the gel strength of Alginic acid, k and γ Carageenans. The complexation with λ-Carageenan solutions shows bulking effects of increasing viscosity or thickening of solutions. These compositions have shown good styling effects on hair, specifically an increase in texture, volume and curl retention.

Example 6—Preparation of Hair Styling Formulation Containing Chitosan/Vanillin/Alginic Acid Complex The formulation was prepared by combining the components in the amounts as set forth in Table H, below.

TABLE H

Chitosan/Vanillin/Alginic Acid complex solution

| Component | Amount (w/w %) |
|---|---|
| Chitosan High Density | 0.30 |
| Vanillin | 0.075 |
| Acetic acid | 1.00 |

TABLE H-continued

Chitosan/Vanillin/Alginic Acid complex solution

| Component | Amount (w/w %) |
|---|---|
| Sodium Alginate | 0.30 |
| Diazolidinyl urea (and) iodopropynyl butylcarbamate (and) propylene glycol | 0.40 |
| Fragrance | 0.10 |
| PPG-26-buteth-26 (and) PEG-40 hydrogenated castor oil (and) water | 0.20 |
| Water Q.S. | 100 |
| pH Q.S. | 3.50 |

Example 7—Preparation of Hair Styling Formulation Containing Chitosan/Vanillin/Alginic Acid/Carrageenan Complex The formulation was prepared by combining the components in the amounts as set forth in Table I, below.

TABLE I

Chitosan/Vanillin/Alginic Acid/Carrageenan complex

| Component | Amount (w/w %) |
|---|---|
| Chitosan High Density | 0.15 |
| Vanillin | 0.038 |
| Succinic Acid | 0.20 |
| λ- Carageenan | 0.15 |
| Sodium Alginate | 0.15 |
| Diazolidinyl urea (and) iodopropynyl butylcarbamate (and) propylene glycol | 0.40 |
| Fragrance | 0.10 |
| PPG-26-buteth-26 (and) PEG-40 hydrogenated castor oil (and) water | 0.20 |
| Water Q.S. | 100 |
| pH Q.S. | 3.50 |

The complex compositions of Example 6, Table H and Example 7, Table I were evaluated on wavy normal and color treated hair. The complex compositions were applied on pre-shampooed clean damp hair, at a ratio of 8:1 (4 g of Hair:0.5 g complex composition) and dried with a dryer at low heat or air dry. The swatches had good texture, volume, shine and memory style retention up to three shampoos, where the control with 0.30% sodium alginate did have minor styling effects that were diminished after one shampoo.

For curl retention the composition of Table H of Example 6 was applied onto normal hair at a ratio of 5:1 (4 g of Hair: 0.8 g complex composition) rolled onto a rod and form the shape or curl after drying at room temperature. The curl was placed into an 85% humidity chamber at 29-30 C for 48 hrs. Only a slight elongation has been observed with the complex treated hair of less than 10% elongation versus 90% elongation with the control.

While the invention has been particularly shown and described herein with reference to specific embodiments, it should be understood by those skilled in the art that various changes in form and detail may be made therein without departing from the spirit and scope of the invention as defined by the appended claims.

What is claimed is:

1. A method of increasing the volume of a fiber comprising: applying to the fiber a chitosan cross linked with an aldehyde-bearing compound, and in a separate step, a polyanion, and
drying the fiber to form a polyelectrolyte complex between the chitosan cross linked with an aldehyde-bearing compound and the polyanion on the fiber that increases the dimension of the fiber wherein the drying step is carried out at about 21° C.

2. The method of claim 1, wherein the increase or a portion of the increase in dimension of the fiber persists on the fiber after about 1 to about 10 washings.

3. The method of claim 1 where the fiber is wetted prior to the step of applying to the fiber the chitosan cross linked with an aldehyde-bearing compound and the polyanion.

4. The method of claim 1, wherein the chitosan of the polyelectrolyte complex is selected from (i) chitosan having a molecular weight of 50,000 to 1,000,000 g/mole and 95% deacetylation, (ii) chitosan having a molecule weight of 300,000 to 2,000,000 g/mole and 95% deacetylation, and (iii) chitosan having a molecular weight of 500,000 to 5,000,000 g/mole and 80% deacetylation.

5. The method of claim 1, wherein the aldehyde-bearing compound is selected from a (i) phenolic aldehyde, and (ii) vanillin and p-vanillin.

6. The method of claim 1, wherein the aldehyde-bearing compound is selected from formaldehyde, benzaldehyde, cinnamaldehyde, glyoxylic acid, acetaldehyde, capraldehyde, piperonal, citral, undecanal, octanal, heptanal, dodecanal, oleic aldehyde, methylnonyl acetic aldehyde, o-vanillin, ethylvanillin, glyoxal, glutaraldehyde and mixtures thereof.

7. The method of claim 1 wherein the polyanion is selected from a sulfo bearing polymer, sulfonate bearing polymer, salts of poly(acrylic acid), salts of poly(methacrylic acid), salts of poly(L-lysine citramide), salts of poly(styrene sulfonic acid) and mixture thereof.

8. The method of claim 7 wherein the salt is selected from a sodium salt and a potassium salt.

9. The method of claim 7 where the sulfonate bearing polymer is polystyrene sulfonate, a copolymer of acrylic acid/acrylamidomethyl propane sulfonic acid and mixtures thereof.

10. The method of claim 1 wherein the polyanion is selected from keratin, hydrolyzed keratin, oxidized keratin, keratin derived materials, and mixture thereof.

11. The method of claim 1 wherein the polyanion is selected from natural gum arabic, xanthan gum, biossacharide gum-4, carrageenan (I), carrageenan (k), carrageenan (λ), alginic acid, pectin, lactobionate, hyaluronic acid, heparin, soybean-soluble polyssacharide, hydroxypropyl guar, carboxymethyl hydroxypropyl guar, carboxymethyl guar, 18-methyl eicosanoic acid, cholesterol sulfate, hydrolyzed collagen and mixtures thereof.

12. The method of claim 1 wherein the polyanion is selected from polystyrene sulfonate, a copolymer of acrylic acid/acrylamidomethyl propane sulfonic acid, keratin, hydrolyzed keratin, oxidized keratin, keratin derived materials and mixtures thereof.

13. The method of claim 1 wherein the fiber is a mammalian hair.

14. The method of claim 1 wherein the fiber is selected from a cotton fiber, a keratin fiber, a linen fiber, a flax fiber, a bamboo fiber, a hemp fiber, a silk fiber, a wool fiber, an anionically charged synthetic fiber and a plant fiber.

15. The method of claim 7 wherein the sulfo bearing polymer is a copolymer of acrylic acid/acrylamidomethyl propane sulfonic acid.

16. The method of claim 1 wherein the polyanion is a mixture of polystyrene sulfonate and a copolymer of acrylic acid/acrylamidomethyl propane sulfonic acid.

\* \* \* \* \*